(12) United States Patent
Savareigo et al.

(10) Patent No.: US 7,006,212 B2
(45) Date of Patent: Feb. 28, 2006

(54) ELECTRICAL CIRCUIT CONDUCTOR INSPECTION

(75) Inventors: Nissim Savareigo, Ashdod (IL); Igor Markov, Hod Hasharon (IL); Dan Zemer, Rehovot (IL)

(73) Assignee: Orbotech Ltd., Yavne (IL)

( * ) Notice: Subject to any disclaimer, the term of this patent is extended or adjusted under 35 U.S.C. 154(b) by 0 days.

(21) Appl. No.: 11/043,981

(22) Filed: Jan. 28, 2005

(65) Prior Publication Data

US 2005/0134842 A1 Jun. 23, 2005

Related U.S. Application Data

(63) Continuation of application No. 10/032,098, filed on Dec. 31, 2001, now Pat. No. 6,870,611, which is a continuation-in-part of application No. 09/939,682, filed on Aug. 28, 2001, now abandoned.

(60) Provisional application No. 60/307,606, filed on Jul. 26, 2001, provisional application No. 60/237,803, filed on Oct. 4, 2000.

(51) Int. Cl.
*G01N 21/00* (2006.01)

(52) U.S. Cl. .............................. 356/237.1; 356/237.5; 250/559.34

(58) Field of Classification Search .. 356/237.1–237.6, 356/601, 614, 625, 627–630, 394; 250/559.08, 250/559.34, 559.2; 348/125–126; 382/8, 382/17
See application file for complete search history.

(56) References Cited

U.S. PATENT DOCUMENTS

| 4,152,723 | A | | 5/1979 | McMahon et al. |
| 4,158,507 | A | | 6/1979 | Himmel |
| 4,240,750 | A | | 12/1980 | Kurtz et al. |
| 4,494,874 | A | | 1/1985 | DiMatteo et al. |
| 4,502,785 | A | | 3/1985 | Truax |
| 4,556,903 | A | | 12/1985 | Blitchington et al. |
| 4,594,001 | A | | 6/1986 | DiMatteo et al. |
| 4,600,951 | A | | 7/1986 | Blitchington |
| 4,601,576 | A | | 7/1986 | Galbraith |
| 4,650,333 | A | | 3/1987 | Crabb et al. |
| 4,657,396 | A | | 4/1987 | Honda et al. |
| 4,674,869 | A | | 6/1987 | Pryor et al. |
| 4,677,302 | A | | 6/1987 | Chiu et al. |
| 4,677,473 | A | * | 6/1987 | Okamoto et al. ........... 348/126 |
| 4,692,690 | A | | 9/1987 | Hara et al. |
| 4,709,156 | A | | 11/1987 | Murphy et al. |

(Continued)

FOREIGN PATENT DOCUMENTS

JP 08-122265 A 5/1996

(Continued)

OTHER PUBLICATIONS

M. Perlmen, "Meeting the Challenge of Microvia Inspection", Orbotech Ltd., Yavne, Israel, 1999, 3 pages.

(Continued)

*Primary Examiner*—Gregory J. Toatley, Jr.
*Assistant Examiner*—Sang H. Nguyen
(74) *Attorney, Agent, or Firm*—Sughrue Mion, PLLC

(57) ABSTRACT

A first inspection functionality is provided to obtain information about a first attribute at a conductor location on an electrical circuit. A second inspection functionality is provided to obtain information about a second attribute at the conductor location. A combination of first attribute information and second attribute information is analyzed to determine an inspection attribute of the conductor at the conductor location. Attribute information may relate to one or more of: reflectance, fluorescence or height.

15 Claims, 13 Drawing Sheets

U.S. PATENT DOCUMENTS

| | | | |
|---|---|---|---|
| 4,899,061 A | 2/1990 | Van Hoek et al. | |
| 4,900,146 A | 2/1990 | Penny et al. | |
| 4,939,379 A | 7/1990 | Horn | |
| 4,943,159 A | 7/1990 | Oetliker et al. | |
| 4,978,224 A | 12/1990 | Kishimoto et al. | |
| 5,004,929 A | 4/1991 | Kakinoki et al. | |
| 5,011,960 A | 4/1991 | Ando et al. | |
| 5,076,697 A | 12/1991 | Takagi et al. | |
| 5,087,121 A | 2/1992 | Kakuchi et al. | |
| 5,088,828 A | 2/1992 | Doemens et al. | |
| 5,105,149 A | 4/1992 | Tokura | |
| 5,166,985 A | 11/1992 | Takagi et al. | |
| 5,192,983 A | 3/1993 | Tokura | |
| 5,216,479 A | 6/1993 | Dotan et al. | |
| 5,267,217 A * | 11/1993 | Tokura et al. | 356/237.1 |
| 5,298,977 A | 3/1994 | Shintani et al. | |
| 5,401,979 A | 3/1995 | Kooijman et al. | |
| 5,408,320 A | 4/1995 | Katagiri et al. | |
| 5,546,189 A | 8/1996 | Svetkoff et al. | |
| 5,617,209 A | 4/1997 | Svetkoff et al. | |
| 5,708,279 A | 1/1998 | Cheng | |
| 5,754,294 A | 5/1998 | Jones et al. | |
| 5,760,893 A | 6/1998 | Raymond | |
| 5,812,269 A | 9/1998 | Svetkoff et al. | |
| 5,815,275 A | 9/1998 | Svetkoff et al. | |
| 5,841,539 A | 11/1998 | Ikurumi et al. | |
| 5,926,266 A | 7/1999 | Dorundo et al. | |
| 6,014,209 A | 1/2000 | Bishop | |
| RE36,560 E | 2/2000 | Svetkoff et al. | |
| 6,028,673 A | 2/2000 | Nagasaki et al. | |
| 6,069,701 A | 5/2000 | Hashimoto et al. | |
| 6,075,605 A | 6/2000 | Futamura et al. | |
| 6,098,031 A | 8/2000 | Svetkoff et al. | |
| 6,166,808 A | 12/2000 | Greve | |
| 6,177,998 B1 | 1/2001 | Svetkoff et al. | |
| 6,246,788 B1 * | 6/2001 | Pattikonda et al. | 382/147 |
| 6,249,347 B1 | 6/2001 | Svetkoff et al. | |
| 6,392,756 B1 | 5/2002 | Li et al. | |
| RE37,740 E | 6/2002 | Chadwick et al. | |
| 6,489,586 B1 * | 12/2002 | Corral | 219/121.6 |
| 6,542,236 B1 * | 4/2003 | Kim | 356/394 |
| 2001/0012107 A1 | 8/2001 | Toh | |
| 2001/0013936 A1 | 8/2001 | Nielsen et al. | |

FOREIGN PATENT DOCUMENTS

| | | |
|---|---|---|
| WO | WO 00/09993 A1 | 2/2000 |
| WO | WO 01/43521 A2 | 6/2001 |

OTHER PUBLICATIONS

Catelogue, "Laservia Inspection: A New Blaser Option for Microvia Inspection", Orbotech Ltd., Yavne, Israel, 1999, 4 pages.

* cited by examiner

ELECTRICAL CIRCUIT CONDUCTOR INSPECTION

CROSS-REFERENCE TO RELATED APPLICATIONS

This application claims the benefit of Provisional Application No. 60/237,803, filed Oct. 4, 2000.

This application is a continuation of U.S. application Ser. No. 10/032,098, now U.S. Pat. No. 6,870,611 filed Dec. 31, 2001, which is a continuation-in-part of U.S. application Ser. No. 09/939,682, filed Aug. 28, 2001 now abandoned.

This application claims the benefit of commonly owned U.S. Provisional Application No. 60/307,606, filed Jul. 26, 2001, which is incorporated by reference, herein, in its entirety.

This application is related to the commonly owned U.S. patent application Ser. No. 10/032,060, now issued as U.S. Pat. No. 6,654,115, entitled "System and Method for Multi-Dimensional Optical Inspection", filed on the same date as this application, and commonly owned by Orbotech Ltd., the disclosure of said application being incorporated by reference, herein, in its entirety, for its useful example of a suitable mode for operation of a height attribute processor.

FIELD OF THE INVENTION

This description generally relates to the field of electrical circuit inspection. More particularly, the field of interest involves systems and methods for fabricating and inspecting electrical circuit conductors in electrical circuits.

BACKGROUND OF THE INVENTION

The production of printed circuit boards is an expensive undertaking, and many extraordinary measures are routinely taken to ensure the highest possible production quality. Automated optical inspection (AOI) harnesses the power, speed, and reliability of computer technology to assist with the task of inspection of printed circuit boards for defects. Existing automated optical inspection (AOI) systems, such as the PC-14 Micro.TM. and Blaser.TM. AOI systems, are available from Orbotech of Yavne, Israel.

As used herein, the term "printed circuit board" will be understood to refer in general to any electrical circuit on any substrate, including printed circuit boards, multi-chip modules, ball grid array substrates, integrated circuits and other suitable electrical circuits.

SUMMARY OF THE INVENTION

A general aspect of the present invention relates to employing a combination of inspection inputs to obtain attribute information about a conductor or other inspected area, and using the combination to make a determination as to an attribute or defect of the conductor.

In one aspect, the width of a conductor along a top surface and the width of a conductor along a bottom surface thereof are used to make a determination as to the presence of a defect in a conductor and/or in a manufacturing process used to fabricate an electrical circuit.

In another aspect, an initial defect determination of a conductor is made in reliance on a first sensed attribute. The initial defect determination is evaluated for its correctness using a second sensed attribute. The first sensed attribute may be, for example, a reflectance or fluorescence attribute and the second attribute may be, for example, a height attribute.

A more particular aspect of the present invention relates to an automated optical inspection system operative to inspect electrical circuits to determine the width of a top surface of conductors forming the circuit at a multiplicity of locations, the width of a bottom surface of conductors forming the circuit at a multiplicity of locations, and the slope of the side walls of conductors, or other defects in the shape of conductor side walls, forming the circuit at a multiplicity of locations.

Another more particular aspect of the present invention relates to a system and method for optically inspecting electrical circuits and estimating or calculating therefrom impedance values for conductors forming the electrical circuit.

Another more particular aspect of the present invention relates to a method of producing printed circuit boards, whereby production and/or fabrication process control decisions (such as whether a defect exists in a conductor or in a manufacturing process) are based on inspection inputs indicative of the conductor dimension along the top surface and bottom surface respectively, or the slope of the sides of conductors.

Another more particular aspect of the present invention relates to a method of producing printed circuit boards, whereby production decisions (such as whether a defect exists in a conductor) are based on inspection inputs indicative of the conductor dimension along either the top surface or bottom surface respectively, which are verified using inspection inputs indicative of some other, typically at least partially independent, attribute, for example height.

The above and other aspects of the invention are achieved by a system, described in detail below, in which a laser scanner is provided to scan a laser beam across an electrical circuit being inspected. The laser produces a beam which has sufficient energy to cause fluorescence (also referred to herein as luminescence) of the substrate on which conductors are formed. In addition, the beam is reflected by copper conductors which typically have a higher work function than the substrate and do not fluoresce under illumination of the laser beam. The reflected and fluorescent light is collected and the respective intensities of the reflective and fluorescent light are analyzed. Fluorescent light provides an indication of the width of a conductor along its bottom surface, while the reflected light (another attribute) provides an indication of the width of the conductor along its top surface. Comparison of the respective widths of the bottom surfaces and top surfaces of the conductors provides an indication of the slope of the side-walls of a conductor.

The top and bottom dimensions can be used in combination to provide an inspection attribute for a single point or at various sampling points along the length of conductors, and can be used for various analyses of characteristics of the electrical circuit. For example, information about the slope of the side walls of conductors may be used to calculate a cross sectional dimension of an electrical circuit at various sampling points which can used to derive an impedance value for a conductor. Additionally, statistical information about uniformity in the respective widths of conductors along their top and bottom surfaces may be used to indicate various flaws in etching processes.

In another aspect of the invention, an inspection system is provided to output an initial defect indication based on an analysis of light reflected by the surface of the electrical surface, analysis of a fluorescent emission from the surface when exposed to laser light, or analysis of any other suitable response to a physical input. The inspection system senses an additional attribute that preferably is independent of the attribute relied upon to output the initial defect indication. For example, the inspection system additionally senses height data related to a topography of the surface of the electrical circuit.

The additional attribute is employed to verify whether a defect identified in the initial defect indication is indeed an actual defect. The additional attribute may be acquired concurrently with operation of the inspection system when outputting an initial defect indication. Optionally, the additional attribute is acquired and analyzed downstream of an initial inspection step.

The additional attribute may be acquired and analyzed for an entire electrical circuit to be inspected. Optionally, the additional attribute may be acquired only at localized regions, for example regions selected in response to initial defect indications.

The above and other aspects of the invention will be more fully understood and appreciated when read in the light of the detailed description provided below, and the enclosed drawings.

DETAILED DESCRIPTION OF PREFERRED EMBODIMENTS

Using the above-identified figures, the invention will now be described with respect to various embodiments of the invention. Although many specificities will be mentioned, it must be emphasized that the scope of the invention is not be taken to be that of only the embodiments described herein, but should be construed in accordance with the claims appended below.

Figure 1:
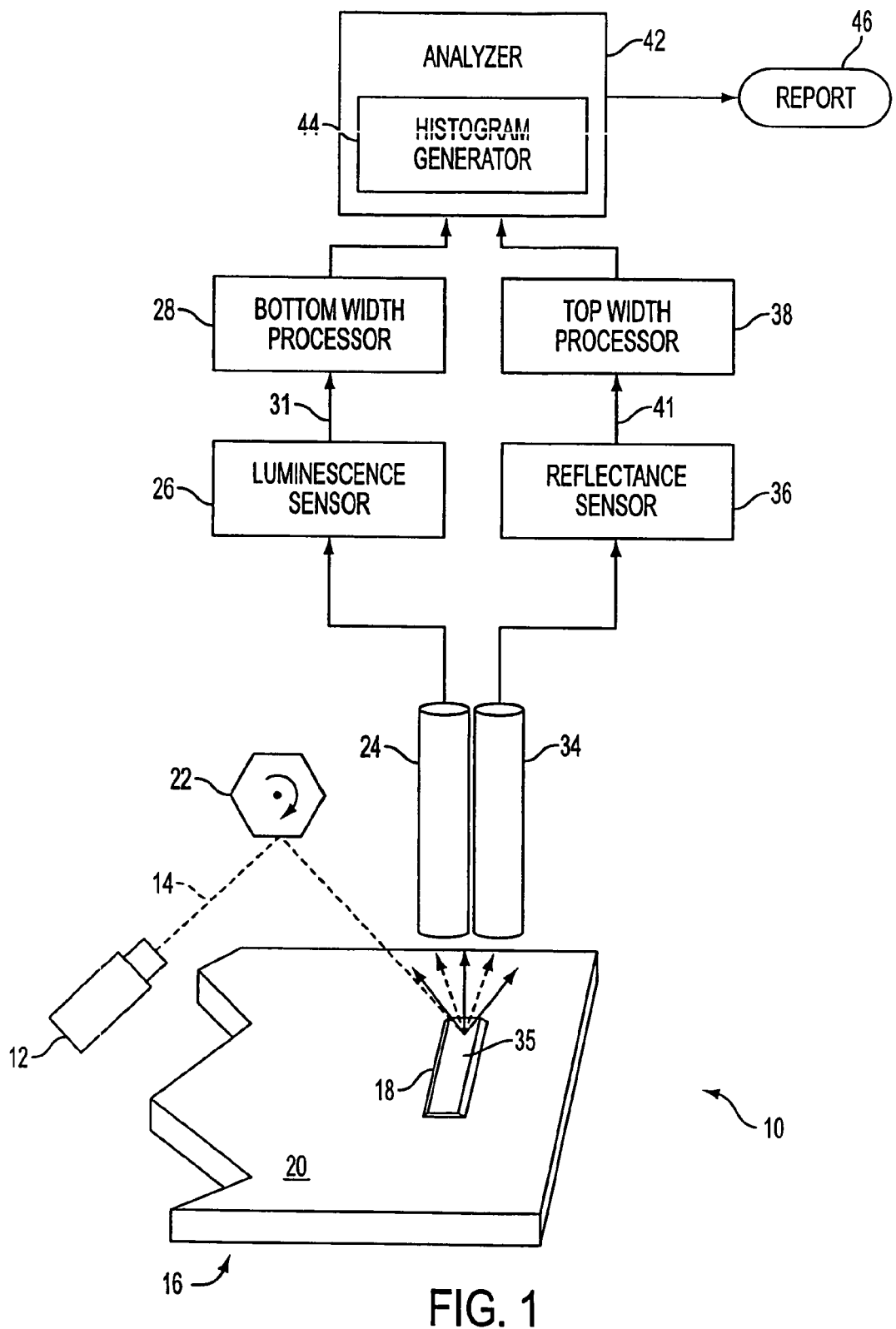
FIG. 1 is a functional block diagram of an automated optical inspection system operative to inspect electrical circuits for defects in accordance with a preferred embodiment of the present invention.

In FIG. 1, automated optical inspection system 10 is operative to inspect electrical circuits for defects in accordance with an embodiment of the present invention.

AOI system 10 suitably is a V-300 automated optical inspection system available from Orbotech Ltd., of Yavne Israel. Such a system is described in U.S. Pat. No. 5,216,479 to Dotan et al., which issued on Jun. 1, 1993, the disclosure of which is incorporated by reference in its entirety for its useful information on optical inspection systems.

In FIG. 1, reference numeral 12 indicates a source of radiant energy; reference numeral 14 indicates a beam of radiant energy; reference numeral 16 indicates a portion of a printed circuit board substrate under inspection; reference numeral 18 indicates a conductor; reference numeral 20 indicates a substrate on which the conductor 18 is disposed; reference numeral 22 indicates a device such as a rotating polygonal mirror that scans the beam 14 across the printed circuit board 16; reference numeral 24 indicates a luminescence (also referred to herein as fluorescence) collector; and reference numeral 34 indicates a reflectance collector.

Operation of certain aspects of system 10 are described in U.S. Pat. No. 5,216,479, and are readily grasped by those familiar with this field. Thus, a highly detailed description of the operation of AOI system 10 is omitted here in favor of a brief overview.

In the embodiment seen in FIG. 1, the source of radiant energy 12 may be a laser, such as any suitable CW or solid state laser, and preferably is a He:Cd laser, available from Kimmon Electric Company of Japan, producing coherent light in the blue spectrum, at about 442 nm. Substrate 20 may, e.g., be a fiberglass or organic substrate or any other suitable substrate employed in the PCB fabrication industry.

The beam 14 is scanned across the circuit portion 16, and the collectors 24 and 34 are kept operationally positioned to collect their respective types of light at the point at which the beam 14 impinges on the circuit portion 16. To this end, it is convenient if the collectors 24 and 34 are linear in a main scanning direction of the beam 14, although this is not essential. The collectors 24 and 34 are shown in FIG. 1, in highly simplified form, as point collectors instead of linear collectors for the sake of ease of illustration.

It will be appreciated that the collectors, sensors, and processors mentioned above may together be thought of as an inspection functionality.

It is also appreciated that the system described in U.S. Pat. No. 5,216,479, referred to above, is merely an example of a suitable mode for carrying out an embodiment of the invention and that any other suitable configuration of an illumination and image acquisition system may be employed. For example, in place of a rotating polygon 22, such as is used in U.S. Pat. No. 5,216,479 suitable optics may be used to project a laser beam so as to continuously illuminate a linear region on printed circuit board substrate. Moreover, any suitable digital or analog sensors may be employed.

Figure 2:
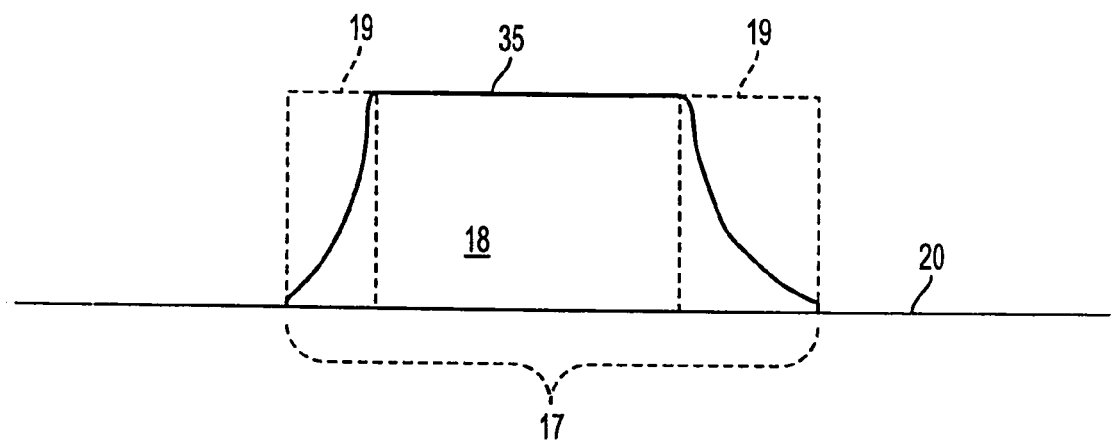
FIG. 2 is a simplified representation of a conductor on a substrate, shown in cross-section.

FIG. 2 shows a cross section of a conductor 18 on a substrate 20. Reference numeral 35 indicates an upper, substantially flat surface of conductor 18. The upper surface 35 of conductor 18 has shoulders 19 on either side of it, sloping down in some shape to the substrate 20. Reference numeral 17 indicates a lower, bottom surface of conductor 18.

The width of conductor 18 at its top surface 35 may be referred to hereinafter as a top surface width, or top width, or also a surface dimension.

The width of conductor 18 at its bottom surface 17 may be referred to hereinafter as a bottom surface width, or bottom width, or also as a footprint dimension.

When beam 14 impinges on the substrate 20 at a location free of conductor 18, a localized part of the substrate fluoresces, giving off luminescent light collected by luminescence collector 24 and sensed by luminescence sensor 26. At such a location, the reflected light given off by substrate 20 is very low because substrate 20 tends to diffuse the light, and a substantially zero value is output by reflectance sensor 36.

When the spot of beam 14 impinges on the substrate 20 at a location where a conductor 18 is present, the conductor does not fluoresce because the work function of the conductor 18 is greater than required to release a photon, due to the quantum effect of illumination by beam 14. Thus, luminescence sensor 26 outputs a substantially zero value. Conductor 18, however, is relatively reflective. Reflectance collector 34 therefore collects reflectance and reflectance sensor 36 outputs a value above zero at such a point.

Figure 3:
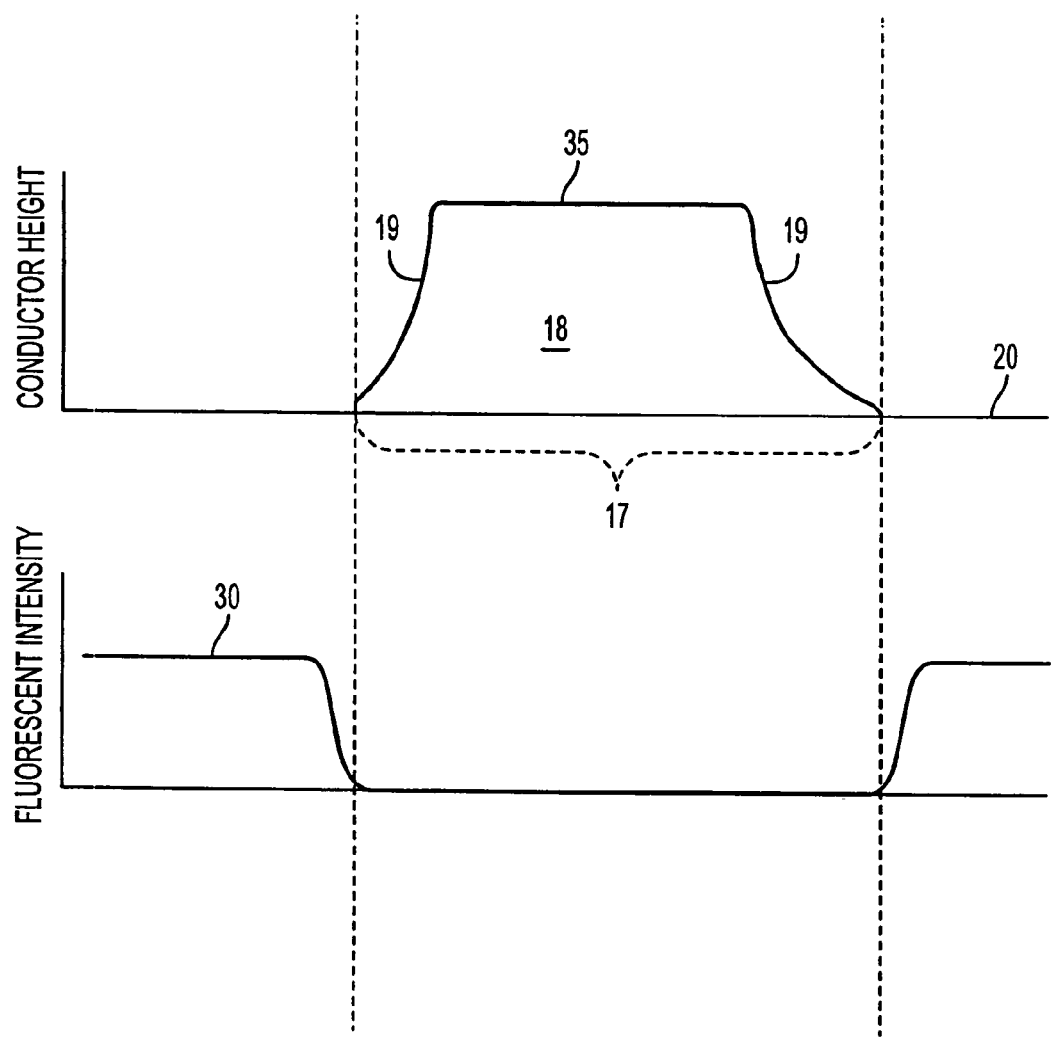
FIG. 3 shows a signal generated in correspondence to an amount of detected luminescent light generated when the conductor and substrate of FIG. 2 are scanned with a laser.

FIG. 3 shows a luminescence signal 30 produced by luminescence sensor 26, indicative of an amount of luminescence emitted by the surface as a beam spot scans over the cross-section of conductor 18 shown. When the beam spot is over the substrate only, the luminescence has a non-zero value. As the spot begins to cross from the exposed substrate to the shoulder portion 19 of the conductor 18, the detected luminescence decreases rapidly. It will be appreciated that, in the example shown, the beam spot in the embodiment shown in FIG. 1 has a finite width, and so as it moves to the shoulder portion 19 from the exposed substrate, the amount of exposed substrate being impinged upon by the beam spot decreases to zero, as does the amount of detectable luminescence. It will also be appreciated that the inspection is not strictly limited to only the conductor itself, but includes also the exposed substrate in the area. The conductor and the exposed substrate in the area may be referred to, for linguistic convenience, as a "conductor location," and a conductor location may comprise several pixels in a digital map 31 or 41 (FIG. 1) of the surface of substrate 20.

Figure 4:
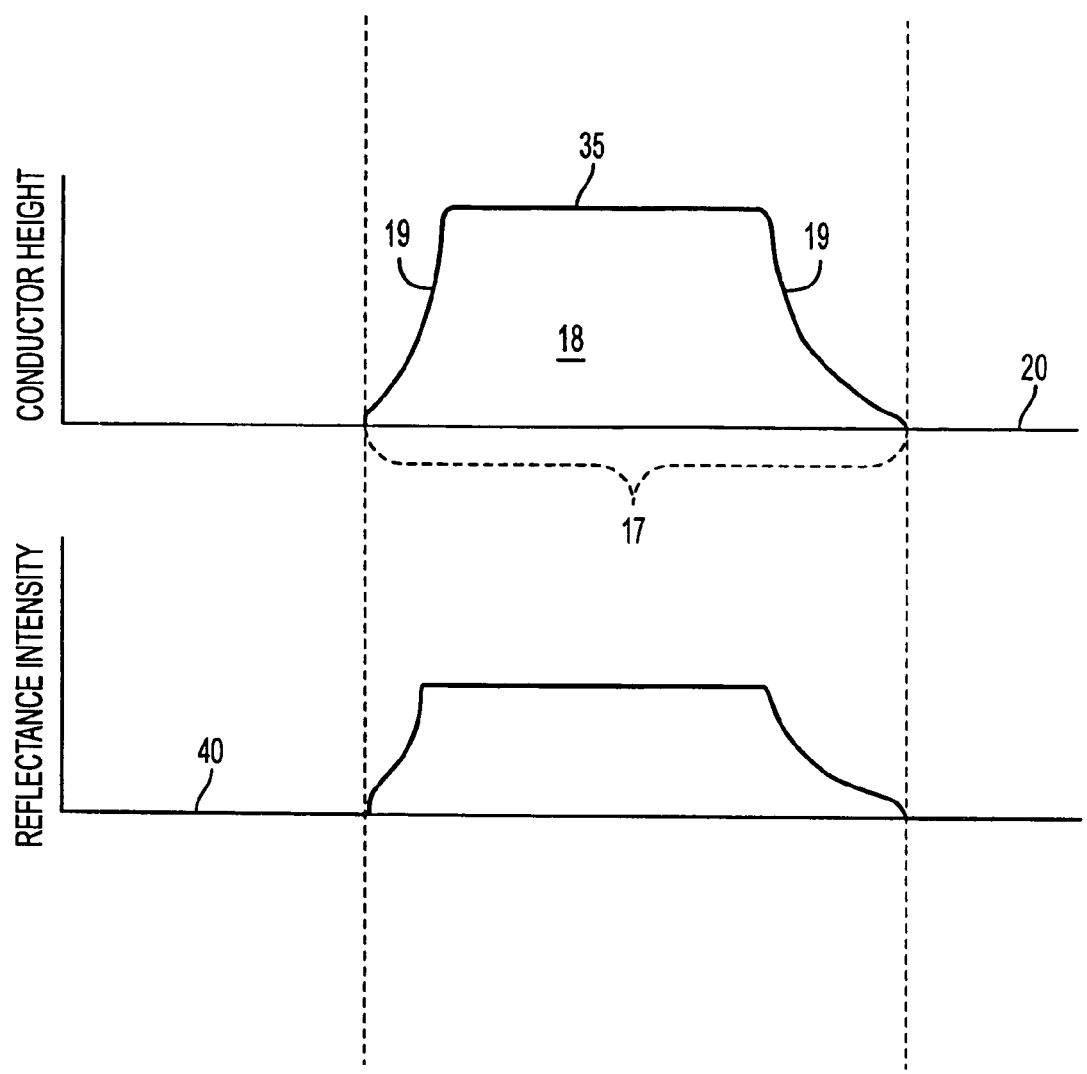
FIG. 4 shows a signal generated in correspondence to an amount of detected reflective light generated as in FIG. 3.

FIG. 4 shows a reflectance signal 40 output by reflectance sensor 36, indicative of an amount of reflectance emitted by the surface as a beam spot scans over the cross-section of conductor 18 shown. When the beam spot is over the substrate only, the reflectance has a substantially zero value. As the spot begins to cross from the exposed substrate to the shoulder portion 19 of the conductor 18, the detected reflectance increases. Depending, inter alia, on the angle of incidence, the reflectance may reach a maximum value when the spot is impinging on only the top surface 35, as shown in FIG. 4. When the spot begins to move from the top surface 35 to the shoulder portion 19, the amount of reflectance that is collected by the reflectance collector 34 decreases quickly, but is greater than zero. This is because the angle of the shoulder portion 19 may reflect some of the light in a direction away from the reflectance collector 34.

In operation, the sensor 26 may include analogue to digital circuitry processing luminance signal 30 to produce a digital image or map 31 (FIG. 1) of luminance values at selected locations on the surface of substrate 20. Digital image 31 is supplied to bottom width processor 28. Likewise, the reflectance sensor 36 may include analogue to digital circuitry processing reflectance signal 40, to produce a digital image or map 41 (FIG. 1) of reflectance values at selected locations on the surface of substrate 20.

The bottom width processor 28 calculates a footprint dimension of one or more conductors 18 at selected conductor locations therealong. This footprint dimension, as can be seen from FIG. 1, is based on the luminance signal 30. The top width processor 38 calculates a top surface dimension of one or more conductors 18 at selected conductor locations therealong. This top surface dimension, as can be seen from FIG. 1, is based on the reflectance signal 30.

The respective outputs of bottom width processor 28 and top width processor 38 may be thought of as different attributes of the conductor, and are provided to an analyzer 42, which may be operative in several modes of operation. In one mode of operation, analyzer 42 calculates a cross section configuration of conductors based on the respective width dimensions measured for the top surface 35 and bottom surface 32 respectively of conductors 18. Analyzer 42 may also be thought of as an attribute analyzer In another mode of operation, analyzer 42 derives the slope of side walls of conductors 18, at one or more locations along a conductor, from the respective top surface width and bottom surface widths of conductors 18 at those locations.

Figure 5:
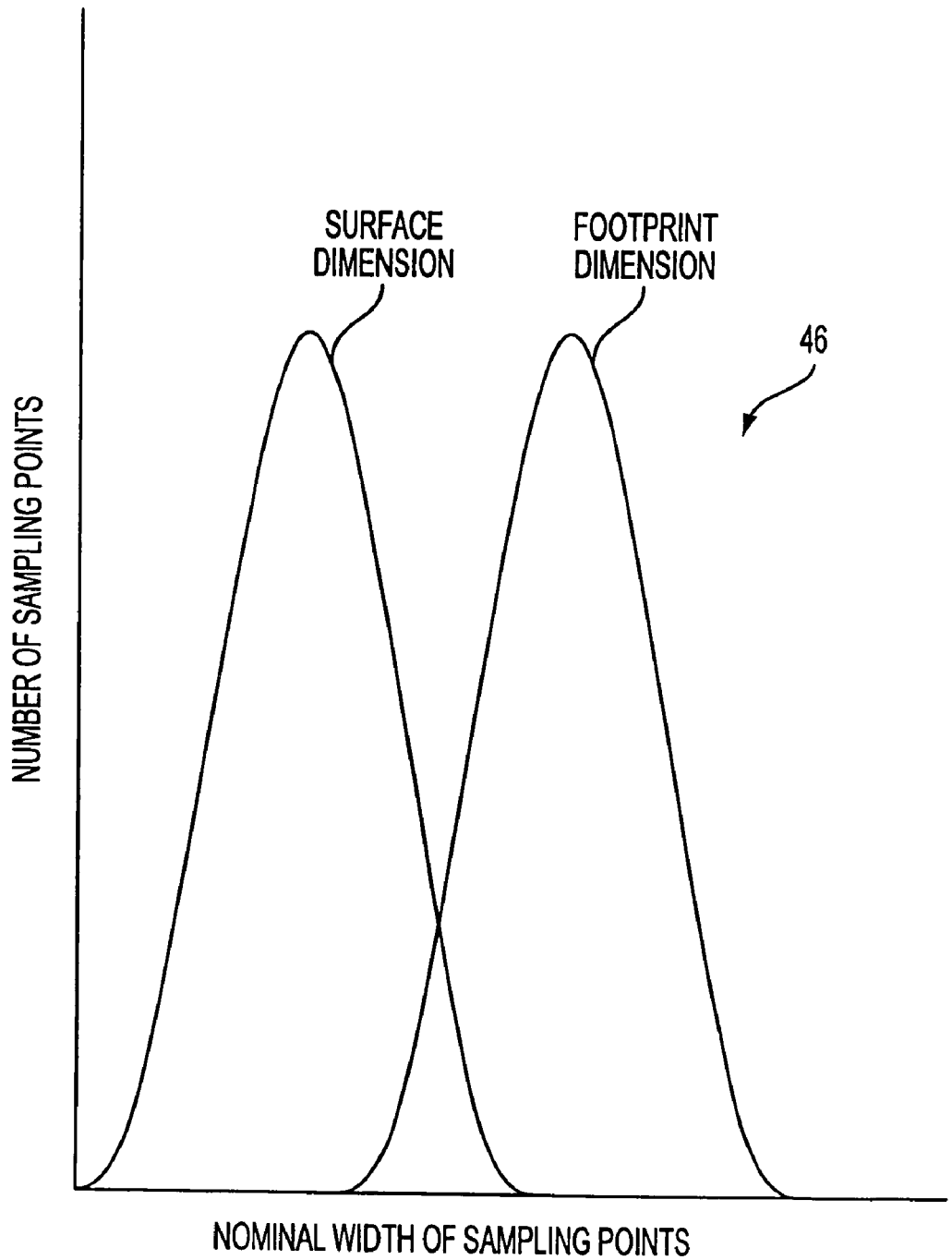
FIG. 5 is a report of distribution of top surface and bottom surface dimension of conductors in an electrical circuit in accordance with a preferred embodiment of the present invention.

In another mode of operation, analyzer 42 analyzes a distribution of top surface widths and of bottom surface widths of conductors disposed along all or part of the surface of substrate 20. Analysis of the distribution of top widths and bottom widths provides information which can be used to control etching processes. In a system configuration enabling this mode of operation, a histogram generator 44 may be included in cross section configuration analyzer 42. Reference is made to FIG. 5 which is a pictorial illustration of a report of the distribution of top surface and bottom surface dimensions of conductors in an electrical circuit in accordance with an embodiment of the present invention.

As seen in FIG. 5, histogram generator 44 produces a statistical report of the respective width distribution of top surfaces and bottom surfaces for predetermined sampling points at selected conductor locations. From the histogram, an average top surface width and an average bottom surface width may be determined, along with other useful statistical calculations. These calculations, and the difference between the top and bottom dimensions, are indicative of a shape of conductors, including a slope of conductor side walls. It will be appreciated that information relating to the shape of conductors is useful for understanding and improving photolithography and/or etching processes that are employed in manufacturing printed circuit boards.

Moreover, information relating to the shape of conductors may be employed, for example, to calculate a nominal impedance of conductors. The nominal impedance may be calculated, or at least estimated, in a manner that will be readily grasped, since impedance is a function of the cross sectional dimension of a conductor.

The cross sectional shape of the conductor can be approximated in various ways, once the surface and footprint dimensions have been determined. For example, it could be assumed that the shoulders were constituted by straight lines, and that the cross sectional shape was a trapezoid. Thus, the cross sectional area of the conductor (and hence, impedance) could be computed in a simplified manner.

Another use of information relating to the cross sectional shape of conductors is to control photolithography and/or etching processes in order to obtain conductors having an optimized shape. Ideally, the top surface dimension 35 of conductors 18 should be slightly smaller than the bottom surface dimension 17 in order to maximize the usage of space along the surface of a printed circuit board substrate 20. Thus if the distribution of top surface width dimensions is too small relative to the distribution of bottom surface width dimensions, then impedance problems are likely to occur since statistically some portions of conductors are likely to have an insufficient volume for efficiently carrying charge. Conversely, if the distribution of top surface width dimensions of conductors is too close relative to the distribution of bottom surface width dimensions, then shoulders 19 (FIG. 2) will typically be bowed inwardly in an exaggerated manner and there will be a high likelihood of cuts along conductors.

It is thus appreciated that analysis of a width distribution report of top width dimensions and bottom width dimensions, as seen in FIG. 5, is useful in adjusting photolithography and/or etching processes in order to optimize the relative dimensions of top and bottom surfaces of conductors 18.

It will be appreciated that the report shown in FIG. 5 is just one possible example of a report 46 that may be generated by the cross section configuration analyzer 42. For example, a report 46 may include an indication of top and bottom width dimensions of conductors at various locations along a conductor.

Figure 6:
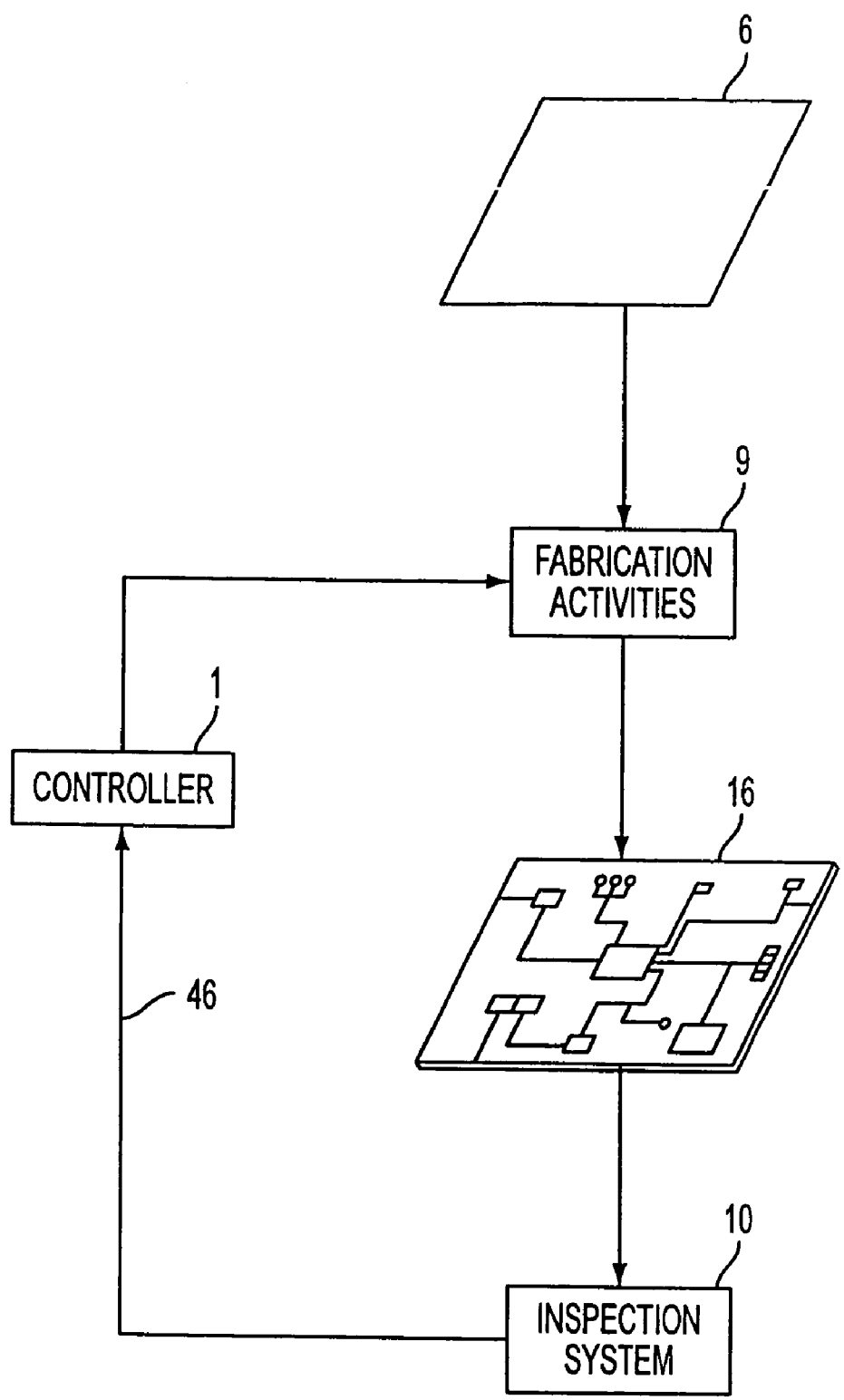
FIG. 6 shows, in highly simplified schematic form, a system for manufacturing electrical circuits according to an embodiment of the invention.

FIG. 6 shows a fabrication and inspection system, in which a controller 1 controls fabrication activities 9 that produce a printed circuit board 16 from input materials 6. The printed circuit board 16 is input to the inspection system 10. The report 46 is provided in a feedback loop to the controller 1. The report 46 may include surface dimension information, and footprint dimension information. The surface dimension information and footprint dimension information may be thought of as a kind of cross-section information. Based on the cross-section information provided to the controller, the controller may, through an automatic or manual process, adjust the assembly activities 9, namely any activities relating to fabrication or assembly of an electrical circuit including the formation of conductors on a substrate, in response thereto. That is to say, the controller may cause equipment used during fabrication activities 9 to be adjusted, so that the assembly activities are performed in a manner that is projected to produce another printed circuit board 16 with more desirable inspection results.

Figure 7:
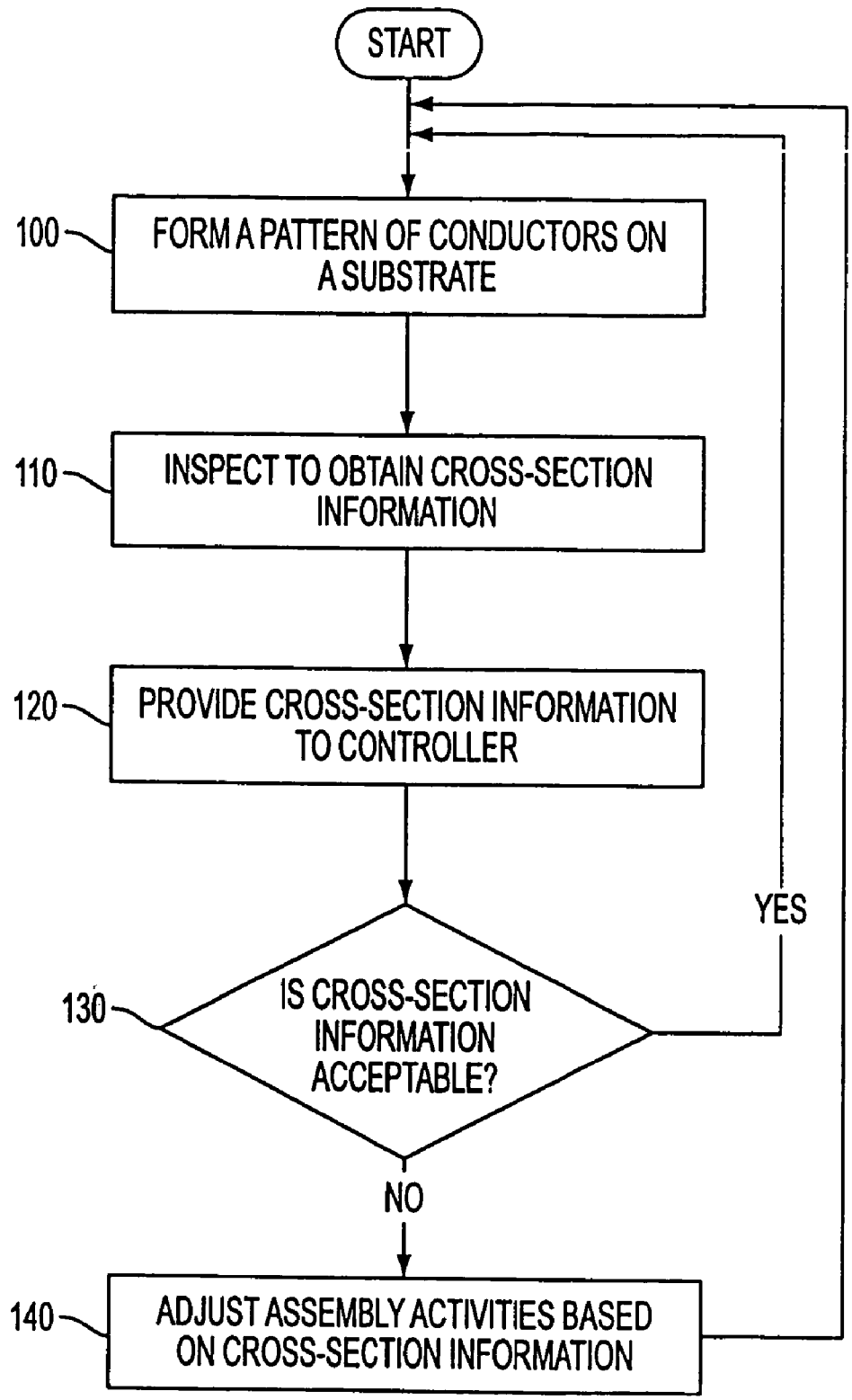
FIG. 7 is a flow diagram for explaining the processing of the system shown in FIG. 6.

FIG. 7 shows a flow diagram that illustrates the steps just described. In particular, in step 100, a conductor is formed on a substrate. At least one conductor is formed, but as many as necessary are formed during assembly activities 9 to produce the desired printed circuit board 16. The printed circuit board 16 is provided to the inspection system 10. In step 110, the printed circuit board 16 is inspected to determine the cross-section information (i.e., the surface dimension and the footprint dimension, and any other cross-section information that may be desired).

The report 46 is produced, containing cross-section information, and provided to the controller 1 in step 120. In step 130, the controller determines whether the cross-section information is acceptable. That is to say, the controller determines whether the cross-section information indicates a problem that needs correction, or does not indicate such a problem. If there is a problem that needs correction, processing continues from step 130 to step 140, in which the controller adjusts the assembly activities based on the cross-section information prior to resuming production at step 100. If there is not a problem that needs correction, processing may continue from step 130 to step 100, and production may continue as before.

Figure 8:
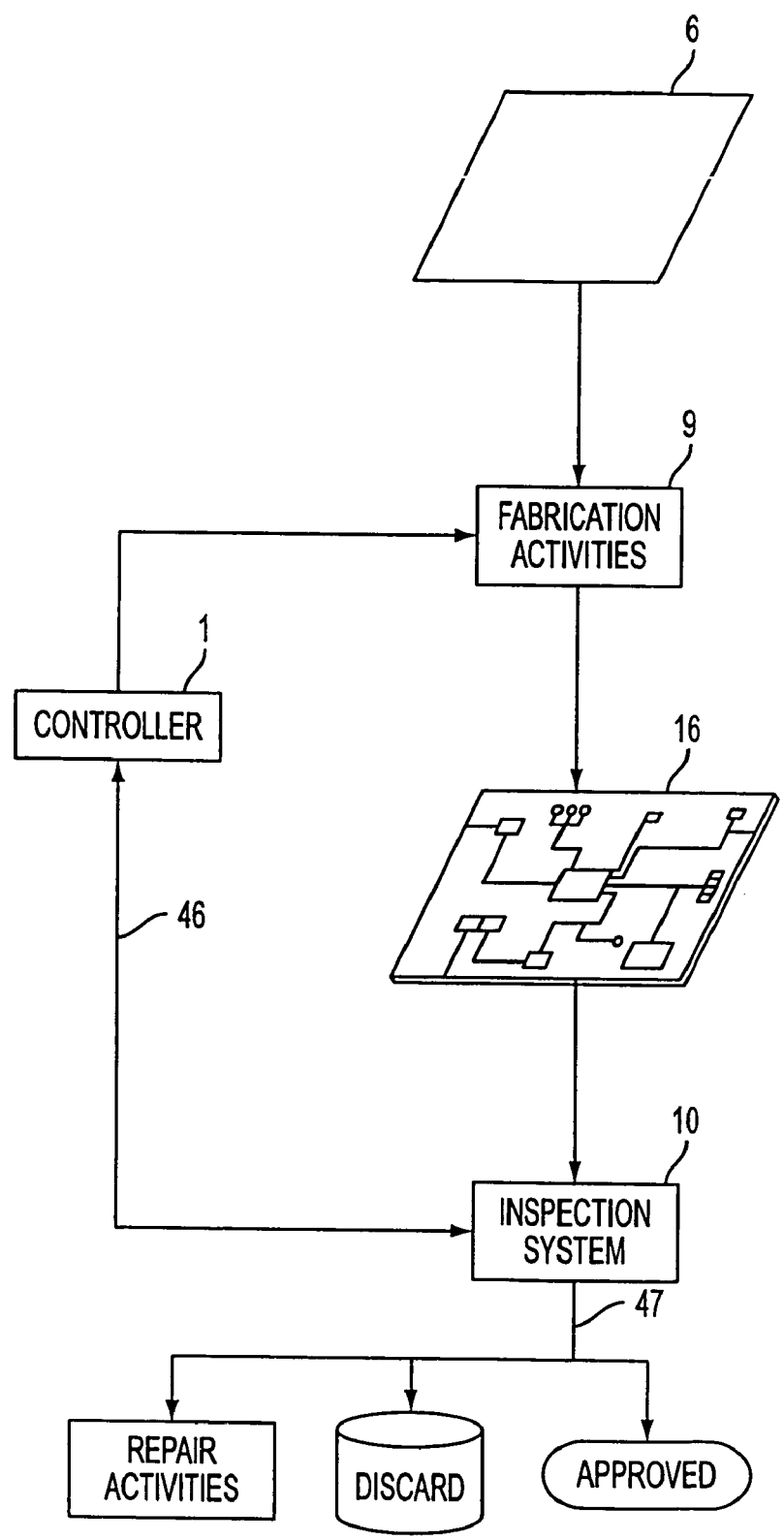
FIG. 8 shows, in highly simplified schematic form, another system for manufacturing electrical circuits according to an embodiment of the invention.

FIG. 8 shows another method of manufacturing electrical circuits, and is similar in many ways to the method illustrated in FIG. 6 except that the report 46 provided by the inspection system 10 is used to determine whether to undertake repair activities, to discard the printed circuit board, or to approve the printed circuit board. It will be appreciated that in this mode of operation, inspection system 10 typically provides an inspection report 47 containing inspection data correlated to specific locations on an inspected printed circuit board substrate 20. This enables a decision making process that facilitates further automatic or manual inspection, or human evaluation, of defective locations, and ultimately the repair of those defective portions of the printed circuit board substrate 20 which are deemed repairable.

Figure 9:
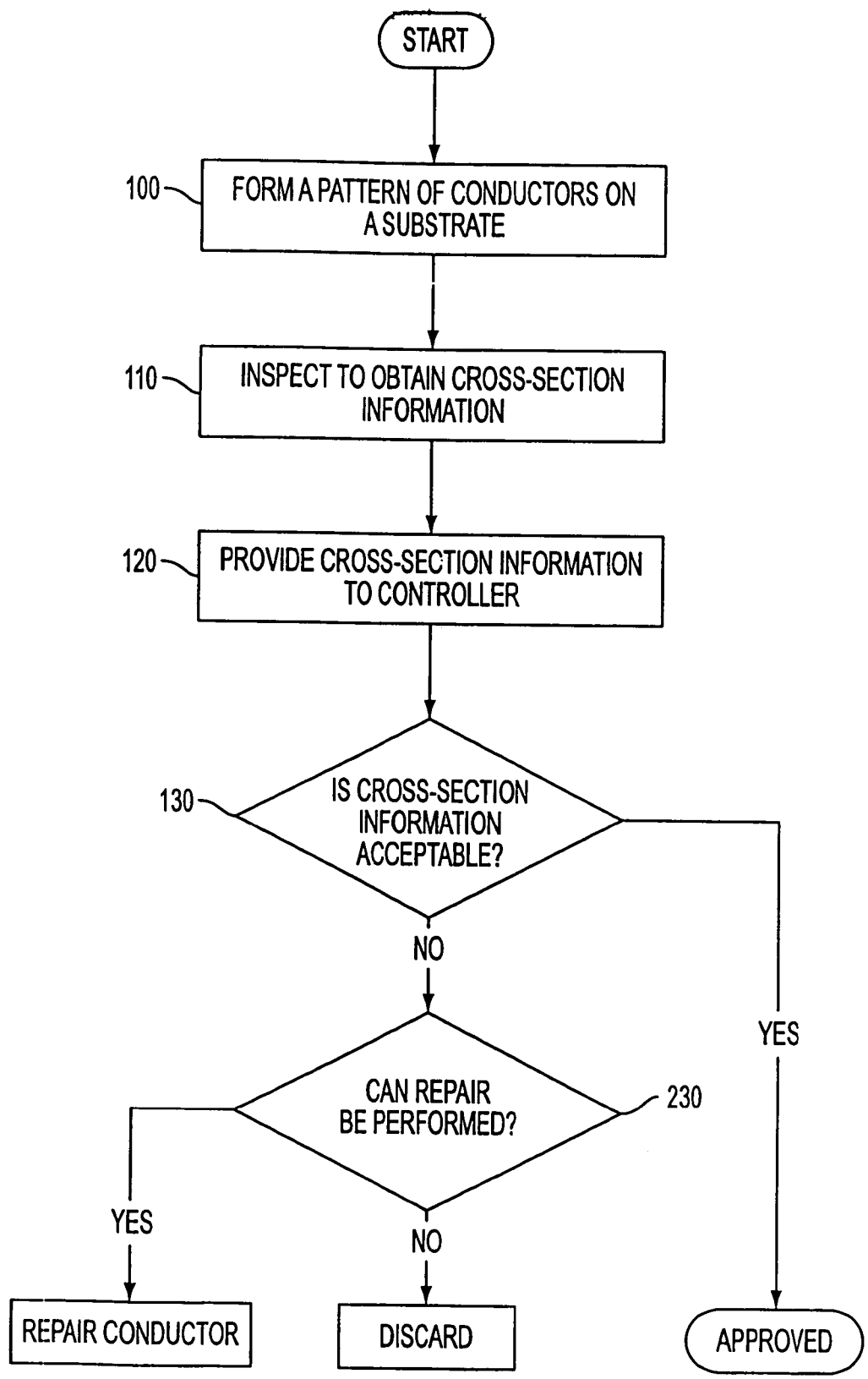
FIG. 9 is a flow diagram for explaining the processing shown in FIG. 8.

FIG. 9 is a flow diagram that illustrates the steps just mentioned. In particular, steps 100–120 are the same as mentioned above with respect to FIG. 7. In step 130, however, if the cross-section information is acceptable, the printed circuit board 16 is approved. On the other hand, if the cross-section information is not deemed to be acceptable in step 130, processing continues to step 230 in which it is determined whether repair can or cannot be performed. If it is determined that repair can be performed, then processing continues with the printed circuit board 16 being repaired in the step indicated as "repair conductor". If it is determined that repair cannot be performed, then the printed circuit board 16 is discarded.

Another way of saying this, is that the circuit is discarded or repaired in response to a determination based on the cross sectional information.

Other exemplary embodiments will now be described with respect to FIGS. 10A–13.

Figure 10A:
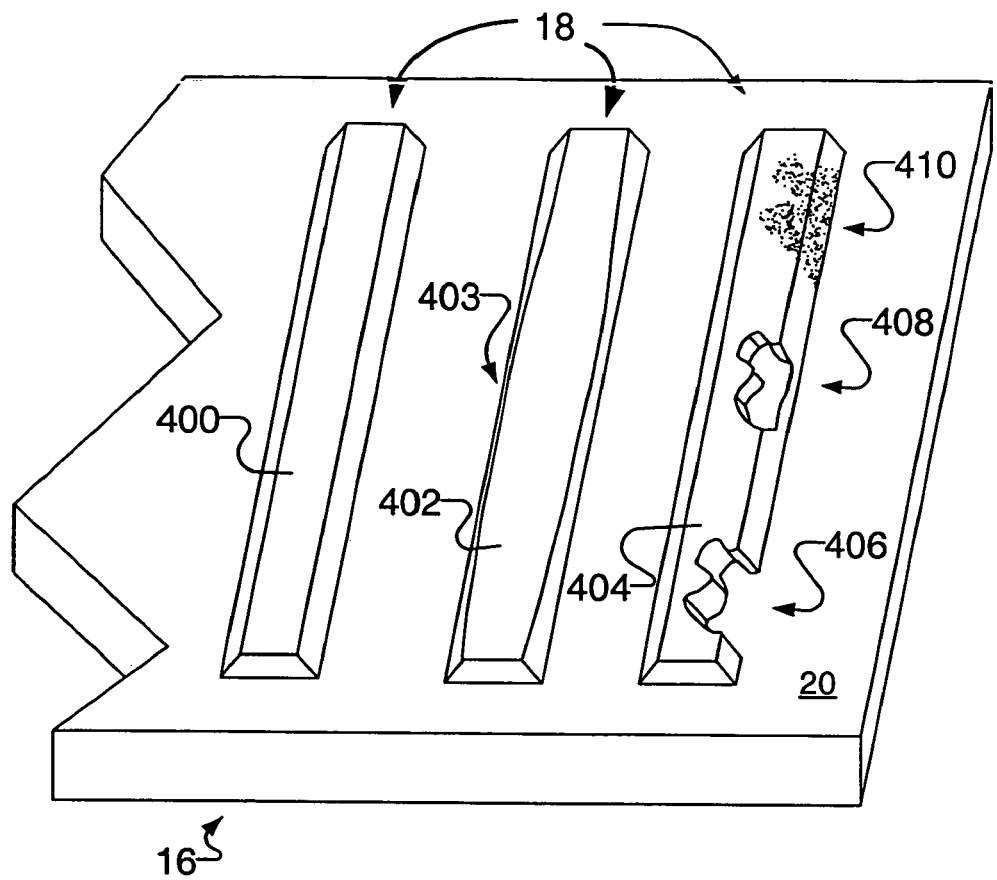
FIG. 10A is a pictorial illustration of conductors on an electrical circuit substrate, and is provided to help explain the operation of a system according to an embodiment of the invention.
Figure 10B:
FIGS. 10B–10D are side view diagrams of conductors seen in FIG. 10A.
Figure 10C:
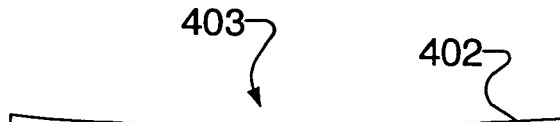
Figure 10D:
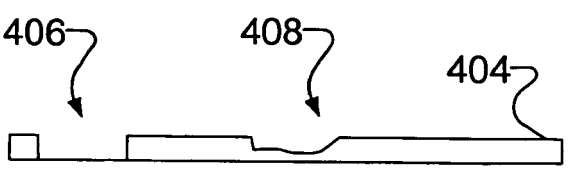

A part of a printed circuit board 16 is shown in FIG. 10A. Side views of conductors shown in FIG. 10A are seen in each of FIGS. 10B–10D. The conductors 18 formed on the substrate 20 include a non-defective segment 400 (a side view of which is seen in FIG. 10B) and defective segments 402 and 404 (side views of which are seen in FIGS. 10C and 10D respectively). Systems configured and arranged in accordance with embodiments of the invention, as described hereinbelow, are operative to detect and distinguish between the various defects seen in FIGS. 10A–10D.

As seen in FIGS. 10A and 10B, non-defective segment 400 has a generally uniform height along its length.

As seen in FIGS. 10A and 10C, defective segment 402 has a non-uniform height along its length characterized by a dished-down portion 403. Such a non-uniform height may affect, for example, impedance, and may be detected using the systems described with respect to FIGS. 1–5. However in such systems, the extent or severity of the defect may not be detected, and it may not be possible to determine the location of such a dished down defect or whether any specific appearance of a dished down portion 403 renders a conductor 18 defective.

As seen in FIGS. 10A and 10D, defective segment 404 has a non-uniform height along its length. The following defects are seen along defective segment 404:

a full nick 406, which is an indentation in a conductor 18 where conductive material should be present but its continuity is interrupted such that substrate 20 is uncovered in the vicinity of full nick 406;

a shallow nick 408 which is a portion of a conductor 18 whereat the continuity of conductive material is at least partially interrupted. The height of the conductor is affected, but not so much as to entirely uncover substrate 20 in the vicinity of shallow nick 408; and Discoloration 410, resulting for example from oxidation of a conductor 18. Typically, discoloration is not a defect. However in some automated optical inspection systems discoloration 410 is falsely determined to be a defect because in a black and white image of reflected intensity its optical attributes may be sufficiently similar to the optical attributes of surface of substrate 20 so that it is not readily possible to distinguish between the two.

Figure 11:
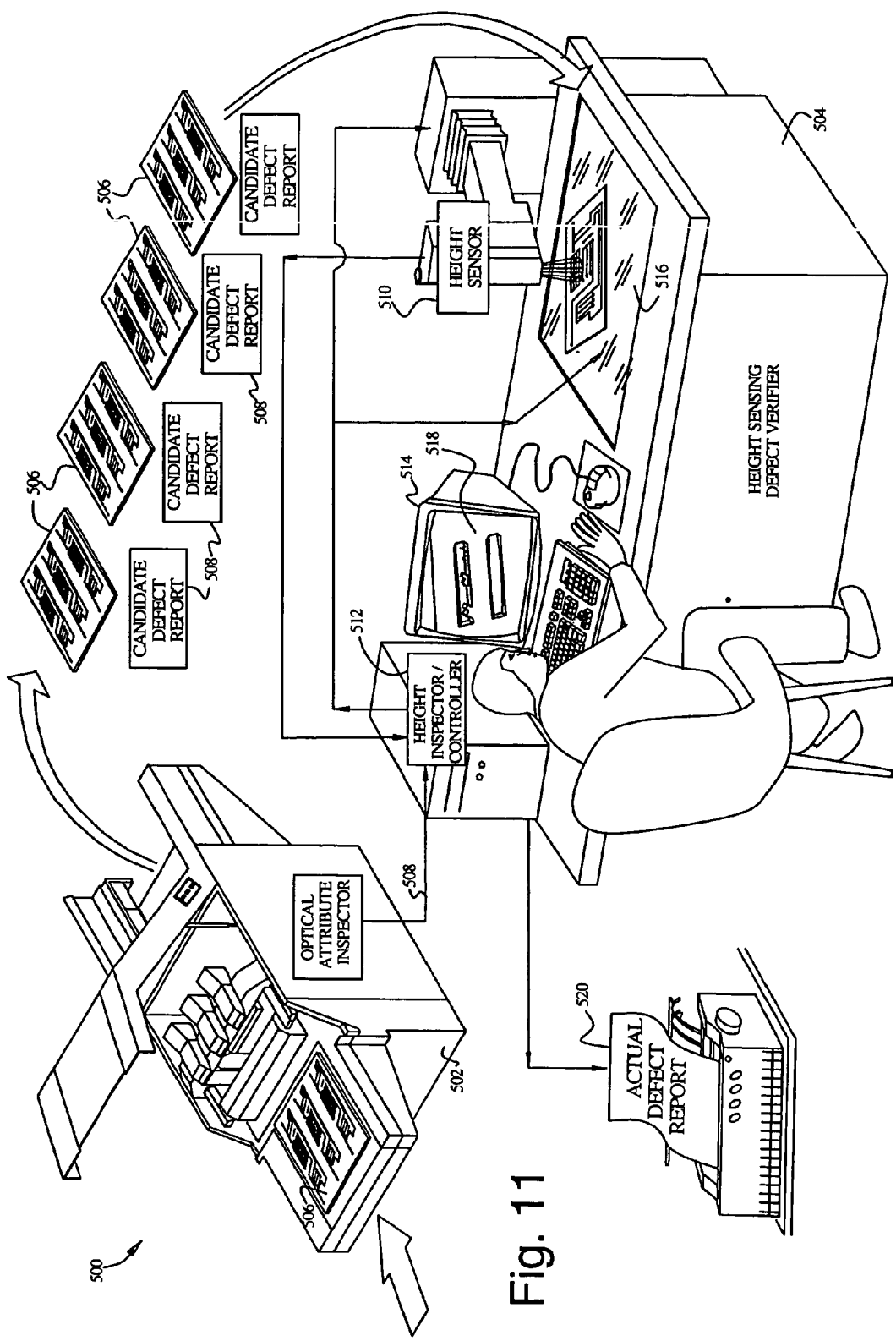
FIG. 11 is a pictorial illustration of a system configured and arranged according to an embodiment of the invention.

Reference is now made to FIG. 11 which is a pictorial illustration of a defect detection system 500, such as an automated optical inspection system, configured and arranged according to an embodiment of the invention. In the embodiment seen in FIG. 11, defect detection system 500 includes an optical attribute inspector 502 and a height sensing defect verification station 504. It is appreciated that while FIG. 1 shows one embodiment of the invention that uses multiple inspection attributes, FIG. 11 shows a different embodiment of the invention that also uses multiple inspection attributes.

In the embodiment of FIG. 11, optical attribute inspector 502 receives an electrical circuit, such as a printed circuit board 506, and inspects the electrical circuit e.g. using any suitable automated optical inspection techniques as known in the art. For each printed circuit board 506 that is inspected, optical attribute inspector 502 generates a candidate defect report 508 indicating locations on a printed circuit board 506 that it has determined to be defective. Suitable optical attribute inspectors include systems that are operative to output an inspection result based on an analysis of the intensity of light reflected by the surface of a printed circuit board (for example the Inspire 9060.TM., and SK-75.TM. AOI systems available from Orbotech Ltd. of Israel), based on an analysis of reflected laser light and/or fluorescent response to laser light by the surface of a printed circuit board 506 (for example the V-300.TM. AOI systems available from Orbotech Ltd. of Israel) or based on analysis of a detectable response of a printed circuit board 506 to any other suitable stimulation.

It is appreciated under various conditions, an optical attribute inspector 502 may output a defect report 508 which includes false indications of defects on a printed circuit board 506 undergoing inspection. In fact, in conventional inspection systems relying only on automated optical inspection, often it is preferable to increase the defect detection sensitivity to ensure that all real defects are found. This however may result in a relatively large quantity of false indications of defects in a candidate defect report 508.

It is a feature of the invention that those locations on inspected printed circuit boards 506 which are indicated by optical attribute inspector 502 as being defective are further analyzed in reliance on a different inspection attribute than the attribute, or attributes, used by optical attribute inspector to generate candidate defect report 508. Although false indications of defects of as described above are not uncommon, using inspection methodologies that rely on multiple inspection attributes helps to reduce false indications of defects.

In the embodiment seen FIG. 11, after inspection by optical attribute inspector 502, printed circuit boards 506 are provided to height sensing defect verifier 504 along with a corresponding candidate defect report 508 as output by optical attribute inspector 502.

Height sensing defect verifier 504 includes a height sensor 510 operative to sense a height of a surface of a printed circuit board 506 at selected locations and a processing unit 512 including controller and height inspection functionalities. It is appreciated that controller and height inspection functionalities may be provided either in separate units, or in a single processing unit 512 as shown. Height sensor 510 may be any suitable height sensor operative to sense surface height and may include a scanner or staring array type sensing unit. Suitable 3-D sensing units operative to output a surface topography map include suitably adapted stereoscopic imaging systems available from Envision Advanced Medical Systems of Petah Tikva Israel, range profiling cameras available from IVP of Sweden, and conoscopic holographic probes available from OPTIMET Optical Metrology Ltd of Jerusalem, Israel.

Optionally, height sensing defect verifier 504 includes a display 514 displaying a three dimensional image of selected locations on the surface of a printed circuit board 506. It is noted that display 514 may be provided in addition to, or in place of, an automated defect detection functionality based on height analysis in processing unit 512. Accordingly, a suitable display enables a human operator to make defect verification decisions based upon review of a 3 dimensional mapping of candidate defect locations, or other locations of interest, on the surface of printed circuit board 506.

Operation of defect detection system 500 proceeds as follows: Locations of interest for height inspection on a printed circuit board 506 to be inspected are supplied to processing unit 512. The locations of interest include locations indicated to be defective by an optical attribute inspector 502 and reported in a candidate defect report 508. Locations of interest for height inspection may additionally include locations that are particularly identified, for example in pre-inspection learning mode, as requiring height inspection. Examples of the types of locations that may be particularly identified include particularly long conductors, or power lines which are sensitive to impedance and for which a height dimension is critical.

The controller functionality of processor unit 512 provides a control signal 515 operative moves either height sensor 510 and/or a stage 516 supporting a printed circuit board 506 so that a location of interest is placed in the field of view of height sensor 510.

Height sensor 510 acquires 3-D image 518 of the location of interest which is then supplied back to processor 512. In accordance with an embodiment of the invention, processor 512 automatically analyzes 3-D image 518 to ascertain whether at location indicated in a candidate defect report the defect is an actual defect or rather a false indication of defect. Actual defects are reported in an actual defect report.

Optionally, image 518 is displayed on a display 514 thereby enabling a human operator to control, or override, an automatic height inspection functionality. In some embodiments of the invention, the automatic height inspection functionality of processing unit 512 is absent, or is not activated, and defect verification decisions are made exclusively by a human operator in reliance on evaluation of a displayed 3-D image 518. In either configuration, ultimately the final determination of whether a defect reported in a candidate defect report is thus the result of analysis of a combination of inspection inputs, which are at least partially independent of each other.

Figure 12:
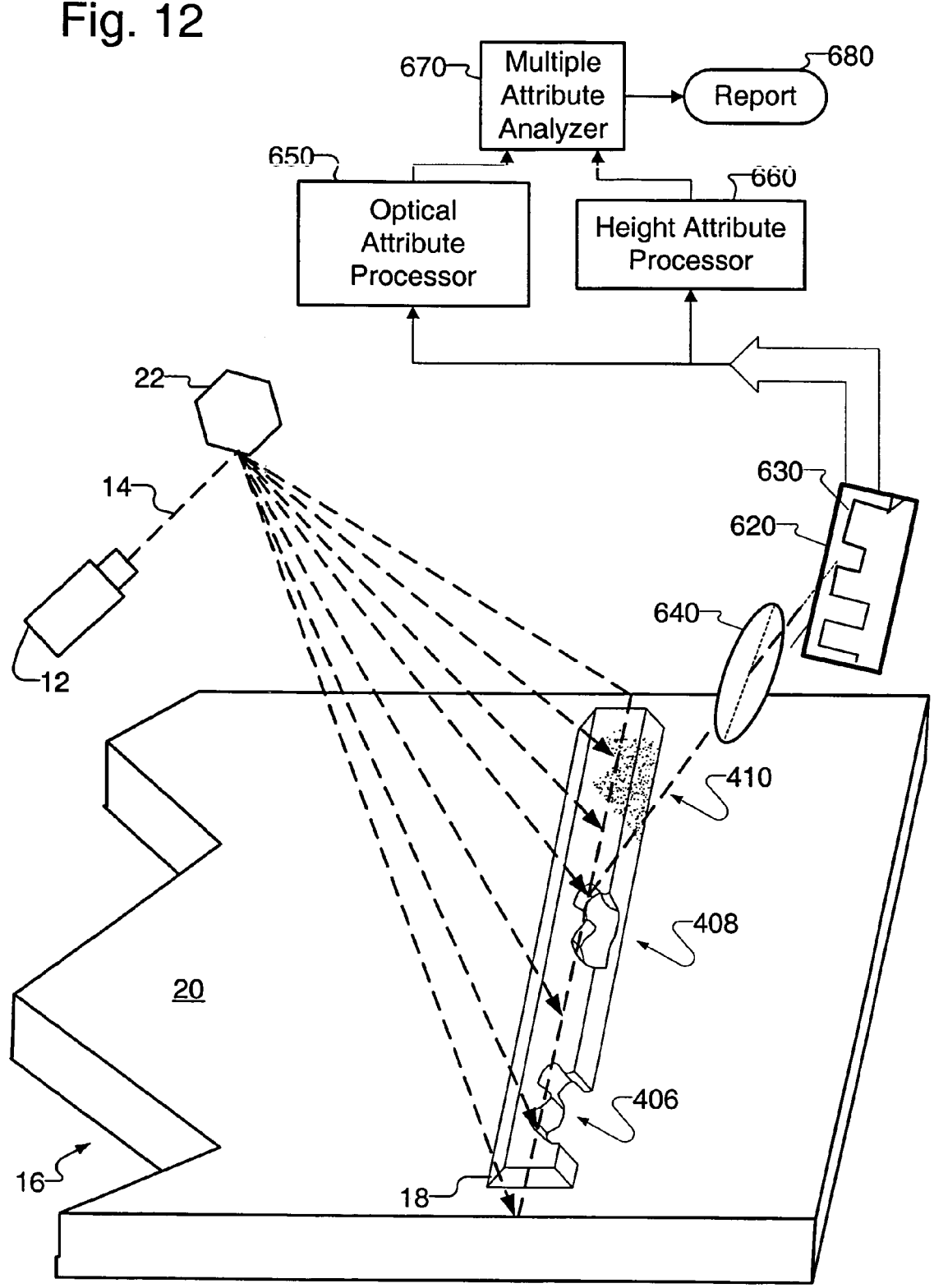
FIG. 12 is a pictorial illustration of a system configured and arranged according to an embodiment of the invention.

Reference is now made to FIG. 12 is a pictorial illustration of system configured and arranged according to another embodiment of the invention for detecting defects based on analysis of a combination of two different inspection attributes. It is appreciated that although FIGS. 1 and 11 show various embodiments of the invention using multiple inspection attributes, FIG. 12 shows still another embodiment of the invention that uses multiple inspection attributes. In FIG. 12, a source of radiant energy 12 such as a laser emits a beam 14 that is scanned across the circuit portion 16 by a scanner 22. In the system shown in FIG. 12, optical information and height information is acquired simultaneously thereby enabling the possibility of generally simultaneously analyzing a combination of optical attributes and height attributes in order to detect defects.

In this example, the inspection functionality includes a sensor 620 that is operative to acquire reflectance and/or fluorescence inspection inputs, and then in addition to acquire a height inspection input. Although sensor 620 may be a single unit, it is appreciated that sensor 620 may optionally include several detection units. In one possible configuration, sensor 620 is a single unit of which a first portion thereof is dedicated to sensing a height detection functionality while a second portion thereof is dedicated to sensing an optical attribute inspection functionality.

In one embodiment of the invention, sensor 620 includes an array of elongated high-speed parallel photosensitive analog detectors, such as photodiodes, configured according to U.S. Provisional Application No. 60/307,606, filed Jul. 26, 2001, which is incorporated by reference, herein, in its entirety, as mentioned above.

In such a configuration, due to the linear arrangement of the photodetector elements in the sensor 620, when the surface being scanned is of substantially uniform height, the image of the beam spot 14 continually impinges on the same photodetector elements (by virtue of optics 640) at such a position that produces a uniform non-zero signal. The other photodetector elements, which are not impinged upon by the image of the spot, output a generally null signal.

When the topology of the surface being mapped is not substantially uniform in height, however, the height of the image of the spot on the sensor changes as a function of the height (or depth) of local non-uniformities (such as in the presence of a conductor) on the surface, in addition to its translation across the sensor. Thus, when the surface is not uniform, the image of the spot impinges on different photodetector elements in the sensor 620, and each of the photodetector elements outputs a modulated non-uniform signal. The instantaneous strength of the signal output by each photodetector elements in the sensor is a function of whether the spot impinges upon the particular photodetector elements and the location of the spot on an element in the cross scan direction.

By sampling the signals output by each of the photodetector elements of the sensor 620 at a particular instant time, the height (or depth) of the surface at that instant of sampling is ascertained by triangulation by determining which photodetector elements in the array is outputting the largest non-zero current. Also, by summing together all of the non-zero currents of the various photodetectors forming sensor 620, at any given time, the overall reflectance can be determined. Thus, it is appreciated, sensor 620 can simultaneously provide at any given location both an indication of height as well as overall reflectance.

Therefore, as the beam 14 scans across the surface of the printed circuit board 16, the sensor 420 can simultaneously acquire a map of the surface based on an intensity of reflectance along with a topographical profiling 630 of the surface being scanned. A sequence of topographical profiles 630 can be combined to form a topographical mapping of the surface of the printed circuit board substrate under inspection 16. Moreover, additional sensors can be provided to acquire a map of fluorescent response to beam 14 as it scans across the surface of printed circuit board 16.

In accordance with an embodiment of the invention, the data acquired by sensor 620 is provided to an optical attribute processor 650 and to a height attribute processor 660. The optical attribute processor 650 is operative to detect defects based on analysis of an optical response, e.g. reflectance and/or fluorescence as know in the art. The height attribute processor 660 is operative to detect defects based on analysis of a height attribute. Height attribute processor 660 may operate on height information provided for an entire printed circuit board 16 under inspection. Optionally, because of the increased resources typically required to conduct height analysis, height attribute processor may operate only on those locations in a printed that are indicated as having suspected defects, for example based on inputs from illumination attribute processor. One suitable mode for operation of a height attribute processor 660 is described in U.S. Pat. No. 6,654,115, mentioned above in the "Related Applications" section of this disclosure, and entitled "System and Method for Multi-Dimensional Optical Inspection."

The results of processing by the optical attribute processor 650 and height attribute processor 660 may be provided to a multiple attribute analyzer 670 which generates a defect report 680 based on a combination of inputs from the different attribute processors.

The results and advantages of multiple attributer processing, for example as performed on conductor segments 18 shown in FIG. 10A by either of the embodiments described with reference to FIGS. 11 and 12, are now briefly reviewed. Non-defective segments of conductor 18 generate a characteristic reflective intensity when subjected to illumination thus enabling mapping of the surface of printed circuit board 20 as known in the art. Likewise, when subjected to suitable laser illumination, substrate 20 fluoresces, while conductors 18 generally do not, thus enabling mapping of the surface of printed circuit board 20 as known in the art. Moreover, non-defective segments of conductors 18 have a detectable characteristic height such that the planar layout of a printed circuit board 16 can be mapped and/or height can be evaluated.

Firstly, it is appreciated that multiple attribute processing may be used to reduce both the quantity of missed defects, namely real defects that are not detected, and to reduce the number of false alarms, namely non-defects that are falsely reported as defects. One way to achieve this result is to increase inspection sensitivity for inspection of a first attribute. This generally results in an increase in the number of reported defects, including falsely reported defects. However, in accordance with an embodiment of the invention, in combination with increasing the sensitivity of analysis of a first attribute, analysis of additional, typically independent, attributes is employed to reduce the number of false alarms.

Moreover, multi-attribute processing provides information otherwise not available when only a single inspection attribute is analyzed.

The full nick defect 406, when exposed to suitable illumination exhibits a reflectance and a fluorescence that are characteristic of the shape of the defect. Analysis of height of full nick defect 406, which is lower than non-defective segments of conductor 18 and is below a minimum required height with reference to substrate 20, namely is generally at the same height as substrate 20, confirms the presence of a defect.

At partial nick defect 408, no defect is detected from the analysis of fluorescence because the footprint of nick defect 408 remains generally unchanged relative to a non-defective conductor portion. When analyzed for reflectance, partial nick 408 may exhibit somewhat of a change in reflectance compared to surrounding non-defective segments of a conductor 18. However, reflectance is dependent on numerous parameters and it may not be possible to repeatedly and accurately detect a partial nick defect solely in reliance on a reflectance response. Nevertheless, by appropriate setting the sensitivity of a reflectance analysis defect detector, the reflected response may be suitable for identifying location of suspected defect that require additional evaluation using a height input. It is noted that partial nick 408 has a height that, at parts, is lower than non-defective segments of conductor 18 but is higher than the height of substrate 20. Such parts may be below a minimum height threshold relative to surrounding substrate 20. Thus height attribute processor may be effective in distinguishing actual partial nick defects from non-defects.

It is appreciated a dished down defect 403 (seen in FIGS. 10A and 10C but not shown in FIG. 12) has a height that is similar to a partial nick defect, however the change is height is more gradual and extends over a longer segment of a conductor 18. The generally locations of suspected dished-down defects may be ascertained using a combination of reflected and fluorescent inputs as described herein above with respect to FIGS. 1–5. However, the presence of an actual defect can be confirmed using height inspection.

It is noted that a defect determination based on height as to whether a partial nick defect 408 or a dished down defect 403 is an actual defect may be made, for example, as a function of the severity of the difference in height relative to a given parameter for a non-defective conductor 18.

At discoloration 410, when analyzed for fluorescence response no defect is identified, which is proper. This is because a mapping of conductor 18 is based on a fluorescent response of substrate 20 surrounding conductors 18, which do not fluoresce when exposed to laser light used in conventional AOI systems. However, when discoloration 410 is analyzed for reflectance response, a suspected defect may be detected because of the reduced reflectance of some discolorations, such as may occur if discoloration due to oxidation. When analyzed for height, because the height of the region of discoloration is generally unchanged relative to a non-defective segment of conductor 18, the presence of a non-defective segment is confirmed. Thus when reflective analysis is combined with height analysis, the presence of a non-defect is confirmed. Moreover, it is noted that by using a combination of multiple inspection inputs, additional information, exceeding the mere sum of each inspection input, may be obtained. Thus, for example, the presence of a region which is not defective, but rather merely discolored, for example by oxidation, may be specifically identified.

It is thus appreciated that evaluation of a combination of inspection attributes may be useful for distinguishing actual defects from non-defects and provides information that is not available when using only a single inspection input. Thus, for example, based solely on reflectance, it may be impossible to determine whether a discoloration 410 is a defect, however in combination with height inspection it becomes clear that discoloration is in actuality a non-defective location on conductor 18. Likewise, an AOI system that primarily an analyzes a fluorescence based attribute may not distinguish a partial nick 408, however in combination with analysis of a height attribute, the presence of a partial nick 408 is readily ascertained and a defect determination can be made based on the severity of the partial nick. Moreover, a system that analyzes only reflectance, or a combination of both reflectance and fluorescence inspection inputs, may be able to determine the presence of a suspected dished down segment 403, however the addition of a height inspection attribute enables localization of the dish-down defect and determination of whether a localized dished-down portion 403 is sufficiently severe to be considered a defect.

Figure 13:
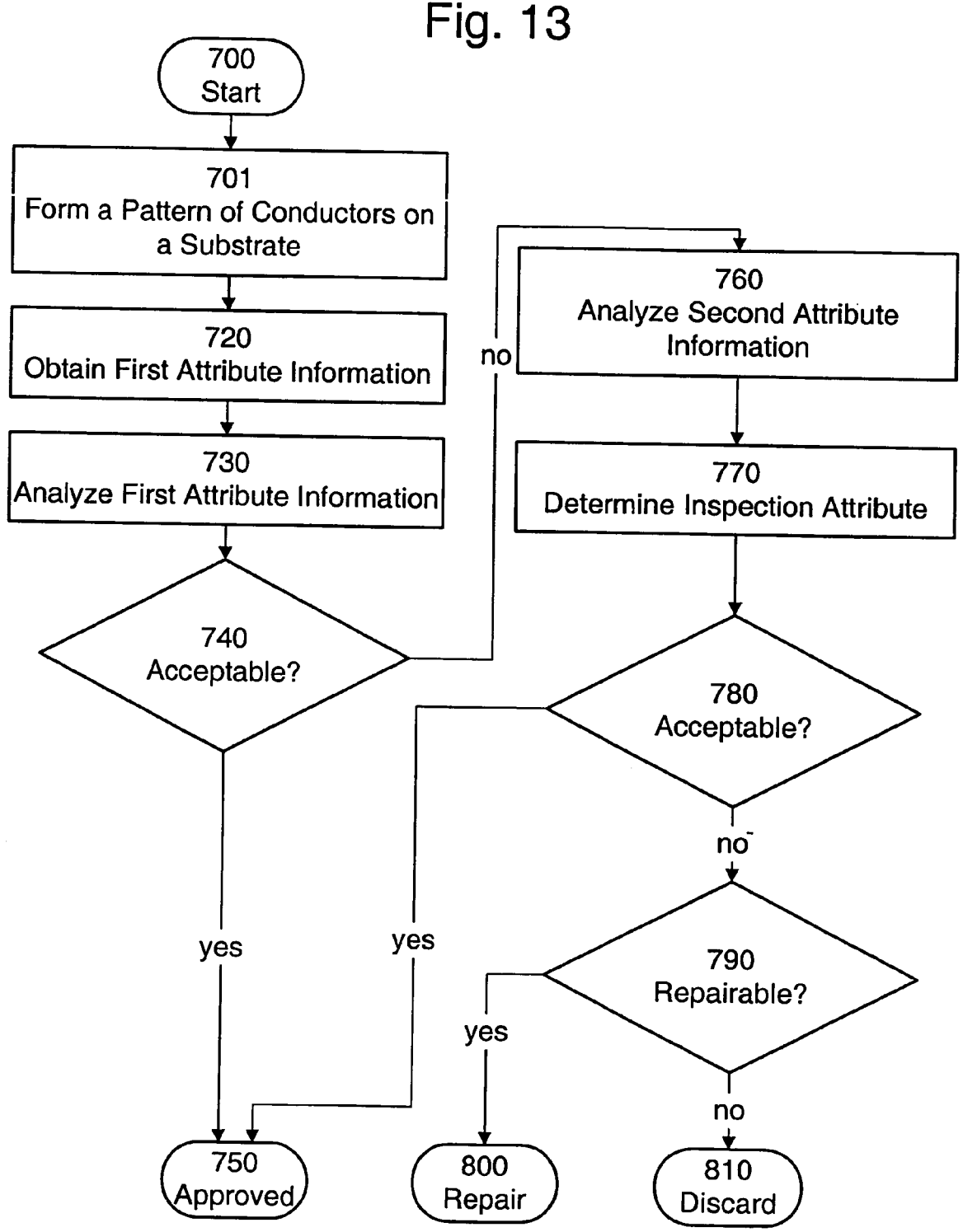
FIG. 13 is a flow diagram explaining an electrical circuit manufacturing process employing the systems of FIGS. 11 or 12.

Reference is now made to FIG. 13 which is a flow diagram showing the operation of an inspection configured in accordance with an embodiment of the invention. Suitable systems have been described herein above with reference to FIGS. 11 and 12. Processing starts at step 700. At step 710, a pattern of conductors is formed on a substrate. First attribute information is obtained at step 720. In this example, the attribute information is the data output by any suitable sensor or sensors.

It will be appreciated that the analysis of the height at a given point involves substantial amount of processing, particularly when compared to the analysis of optical attributes.

According to this example, therefore, to achieve improved inspection throughput, only the amount of illumination reflected from the surface and/or a fluorescent response to laser illumination (i.e., first attribute information) is initially processed and analyzed at step 730. If analysis of illumination (or fluorescence) for a location is as expected, for example based on comparison to a reference, then the determination at step 740 is that the conductor is acceptable. If analysis of illumination (or fluorescence) shows a result different from that expected, however, then there might be a defect such as full nick defect 406, a defect such as a partial nick defect 408 or a dished-down defect 403, or a discoloration 410 at the area, even though it is properly formed.

Therefore, when the amount of illumination at a given point is different from expected, processing proceeds to step 760 where height information (i.e., the second attribute information) is obtained, and analyzed at step 770. At step 780, if the height at the point being inspected is the height expected, then it is determined that there is no defect (i.e., the inspection attribute of whether there is a defect or not is determined to be in the negative). If the height at the point being inspected is not the height expected, then it is determined that there is a defect (i.e., the inspection attribute of whether there is a defect or not is determined to be in the affirmative). It is appreciated that analysis of first attribute information may be acquired generally simultaneously, as described with respect to FIG. 12, or serially as described with reference to FIG. 11.

Once analysis of a printed circuit board is completed then for each location height information is deemed not acceptable, then at step 790 the possibility of repair is considered. If a location is repairable then it is repaired at step 800. However, if any location on printed circuit board is not repairable, then at step 810 it is discarded.

It is appreciated that in the methodologies described herein above, the final defect determination is not based on just one attribute information, but rather it is based on a combination of optical response attribute information (i.e., first attribute information) and the height attribute information (i.e., second attribute information).

It is further appreciated that when optical response attribute information and height information are generally simultaneously acquired, then the height information used by the height attribute processor 660 may be suitably buffered so that it remains available in the event that the acceptability determination at step 740 results in a negative determination.

It is also appreciated, as noted above, that the analysis of the first attribute information and the second attribute information may be performed in parallel, depending on the processing power available and the speed of the inspection. Thus, instead of making a first acceptability determination at step 740, the inspection attribute could be determined prior to making any such acceptability determination.

It is still further appreciated that the system shown in FIG. 1 is also a kind of system that can be thought of as a multiple attribute inspection system in which the luminance and reflectance information constitute first and second attribute information.

Besides using luminance, reflectance, and height information, other types of attribute information will occur to those familiar with this field.

It will be appreciated by persons skilled in the art that the present invention is not limited by what has been particularly shown and described herein above. Rather the scope of the present invention includes both combinations and subcombinations of the features described herein above as well as modifications and variations thereof which would occur to a person of skill in the art upon reading the foregoing description and which are not in the prior art.

What is claimed:

1. An electrical circuit inspection apparatus comprising:
    a first inspection functionality operative to obtain first attribute information with respect to a first attribute associated with a conductor location on an electrical circuit;
    a second inspection functionality operative to obtain second attribute information with respect to a second attribute associated with said conductor location on said electrical circuit, said second attribute being different from said first attribute;
    and a conductor attribute analyzer receiving said first attribute information and said second attribute information and providing a defect indication for a conductor location whereat a defect is indicated in said first attribute information and additionally indicated in said second attribute information.

2. The electrical circuit inspection apparatus according to claim 1, wherein said first inspection functionality senses reflectivity at said conductor location as a basis for said first attribute information.

3. The electrical circuit inspection apparatus according to 2, wherein said second inspection functionality senses luminescence at said conductor location as a basis for said second attribute information.

4. The electrical circuit inspection apparatus according to claim 1, wherein said second inspection functionality senses luminescence at said conductor location as a basis for said second attribute information.

5. An electrical circuit inspection method comprising:
    obtaining first attribute information for a first attribute associated with a conductor at a plurality of conductor locations on an electrical circuit;
    obtaining second attribute information for a second attribute associated with a conductor at said plurality of locations, said second attribute being different than said first attribute; and
    determining a conductor defect at one or more of said conductor locations, said determining comprising:
    identifying a first conductor structure from said first attribute information;
    additionally identifying a second conductor structure from said second attribute information; and
    outputting a defect indication for locations whereat said first conductor structure and said second conductor structure are indicative of a defect.

6. The electrical circuit inspection method according to claim 5, wherein said obtaining of said first attribute information comprises sensing a reflectivity value.

7. The electrical circuit inspection method to 6, wherein said providing of said second attribute information comprises sensing a luminescence value.

8. The electrical circuit inspection method according to claim 5, wherein said obtaining of said second attribute information comprises sensing a luminescence value.

9. The electrical circuit inspection method according to claim 5, and wherein said obtaining of said second attribute information comprises sensing a height value.

10. The electrical circuit inspection method according to claim 9, wherein said obtaining of said second attribute information further comprises sensing said height value based on a topographical profile.

11. The electrical circuit inspection method according claim 5, further comprising employing said inspection attribute to determine a defect in a process used to fabricate said electrical circuit.

12. The electrical circuit inspection method according to claim 5, further comprising making a production determination based on said inspection attribute.

13. The electrical circuit inspection method according to claim 12, wherein said production determination is one of:
    approving said electrical circuit;
    discarding said electrical circuit; and
    repairing said electrical circuit.

14. The electrical circuit inspection method according to claim 5, wherein said first conductor structure corresponds to a different part of a conductor than said second conductor structure.

15. The electrical circuit inspection method according to claim 5, wherein said first conductor structure corresponds to the same part of a conductor as said second conductor structure.

* * * * *